(12) United States Patent
Reading

(10) Patent No.: US 6,932,784 B1
(45) Date of Patent: Aug. 23, 2005

(54) PROTECTIVE AND INSULATING COVER FOR AN INJURED LIMB

(76) Inventor: Debra J. Reading, 195 N. Signal Hill Rd., Barrington, IL (US) 60010

( * ) Notice: Subject to any disclaimer, the term of this patent is extended or adjusted under 35 U.S.C. 154(b) by 15 days.

(21) Appl. No.: 10/932,290

(22) Filed: Sep. 2, 2004

(51) Int. Cl.⁷ .............................................. A61F 13/00
(52) U.S. Cl. .......................................... 602/61; 23/27
(58) Field of Search .............................. 602/23, 61, 11, 602/13, 14, 27, 60, 62; 128/82, 83.5; 36/110, 36/11.5, 37, 69, 81, 4

(56) References Cited

U.S. PATENT DOCUMENTS

| | | |
|---|---|---|
| 3,497,875 A | 6/1968 | Rivera |
| 3,820,254 A | 6/1974 | Kupacki |
| 4,005,704 A | 2/1977 | Stohr |
| 4,043,326 A | 8/1977 | Little et al. |
| 4,094,312 A | 6/1978 | Whyte |
| 4,363,317 A | 12/1982 | Broucek |
| 4,523,586 A | 6/1985 | Couri |
| 4,646,727 A | 3/1987 | Chambers |
| 4,649,656 A * | 3/1987 | Cox et al. ........................ 36/4 |
| 4,769,928 A * | 9/1988 | Ward ........................... 36/114 |
| 4,966,135 A | 10/1990 | Renfrew |
| 4,986,265 A | 1/1991 | Caponi |
| 5,070,630 A | 12/1991 | Edmundson |
| D339,422 S | 9/1993 | Williams |
| 5,452,527 A | 9/1995 | Gaylord |
| 5,643,183 A | 7/1997 | Hill |
| 5,720,712 A | 2/1998 | Joy et al. |
| 5,827,210 A | 10/1998 | Antar et al. |
| 5,882,320 A | 3/1999 | Peterson |
| 6,126,621 A | 10/2000 | Aceves |
| 2003/0191419 A1 | 10/2003 | Melin et al. |

* cited by examiner

Primary Examiner—Henry Bennett
Assistant Examiner—Shumaya B. Ali
(74) Attorney, Agent, or Firm—Matthew R.P. Perrone, Jr.

(57) ABSTRACT

A protective and insulating cover for an injured limb, especially a foot or a leg, is formed from fleece or other material, which is stretchy and warm with a double layer of material at the toes and hook and loop fasteners at the top, thereby forming a cast cover, which is warm, easily applied and removed, adjustable, and decorative.

1 Claim, 6 Drawing Sheets

US 6,932,784 B1

PROTECTIVE AND INSULATING COVER FOR AN INJURED LIMB

PROTECTIVE AND INSULATING COVER FOR AN INJURED LIMB

This invention relates to a cover for an injured limb, and more particularly, to a temporary protective cover for use on a limb, such as a leg temporarily covered by a cast or ace bandage.

BACKGROUND OF THE INVENTION

Many people suffer limb injuries. Anyone who breaks, sprains, or otherwise injures a foot, leg, or ankle must wear a protective item such as a cast or an ace bandage over the injured area. Each of these protective items can interfere with the wearing of normal foot wear such as a sock or a shoe. Furthermore, people who have bunions may not comfortably be able to wear normal foot apparel. One problem that a person, who wears such a protective item frequently encounters, is that exposed body part can get cold or dirty.

In order to solve the problem of exposure, many cast covers are known. These other cast covers, which exist on the market, do not have the combination of necessary traits, which solves the problems of protection from dirt and cold.

A protective cast cover must have at least six desirable qualities. Firstly, it must protect the toes or other exposed areas from cool or inclement weather. Secondly, it must keep the exposed body parts and the (usually white) cast as clean as possible.

Thirdly, a cover must be easily be put on and removed in a manner that reduces foot movement as much as possible. Fourthly, any cover must accommodate walking casts with rubber soles in the bottom. Fifth, the cover must be able to adjust to the size of the cast so it is not bulky or unsightly. Sixth, the cover must be washable, in order to be effectively reusable.

If all of these features are maximized, the desired durability of the cover may not be obtained. In fact, to maximize all of the desired traits, while not sacrificing the other desirable traits, can result in a very useful protective cover.

SUMMARY OF THE INVENTION

Among the many objectives of this invention is the provision of a cast cover, that keeps the exposed areas of the body warm and dry in cool or inclement weather.

A further objective of this invention is the provision of a cast cover that keeps the cast and exposed areas of the body clean.

Yet a further objective of this invention is the provision of a cast cover that is easily applied and removed so that foot movement and pain are reduced as much as possible.

Still a further objective of this invention is the provision of a cast cover which can accommodate walking casts with rubber soles.

Another objective of this invention is the provision of a cast cover which can adjust to different sizes of casts so it is not bulky or unsightly.

Yet another objective of this invention is the provision of a cast cover that is washable.

Still, another objective of this invention is the provision of a cast cover which is breathable.

Also, an objective of this invention is the provision of a cast cover which is durable.

These and other objectives of the invention (which other objectives become clear by consideration of the specification, claims and drawings as a whole) are met by providing a protective and insulating cast cover made from fleece or other material which is stretchy and warm with a double layer of material at the toes and hook and loop fasteners at the top, thereby forming a cast cover, which is warm, easily applied and removed, adjustable, and decorative.

BRIEF DESCRIPTION OF THE DRAWINGS

Throughout the figures of the drawings, where the same part appears in more than one figure of the drawings, the same number is applied thereto.

DESCRIPTION OF THE PREFERRED EMBODIMENTS

In accordance with the present invention, a protective and insulating cast cover is provided. Any material that is warm, stretchy, washable, breathable, and durable is suitable for the protective and insulating cast cover. Furthermore, a lighter weight material such as cotton is suitable for a cover designed solely to keep the cast clean and decorated. In a preferred form, the cast cover has a composition involving a single layer of material covering most of the cast or injured limb, with a double layer of material covering the toes or other exposed areas of the limb.

However, for a cover designed to accommodate a walking cast, a cut must be made in the sole of the cover. A useful material must not fray or otherwise be weakened when cut. A fleece material is the most preferred choice because it does not fray when cut.

The cast cover or cover for an injured limb of the present invention combines into one design many of the advantages, which combination is lacking in the prior art. Unless otherwise specified, cast cover and cover for an injured limb are used interchangeably.

There are at least six outstanding advantages of this cast cover. First, the cast cover protects exposed areas of the limb from cool or inclement weather. Second, the cast cover helps to keep exposed areas of the limb clean. Third, the cast cover is easily put on and removable to prevent pain and movement in the foot. Fourth, a fleece cast cover can be cut to accommodate a walking cast without fraying. Fifth, the cast cover can adjust to different sizes of casts so that it is not bulky or unsightly. Sixth, the cast cover is washable.

Figure 1:
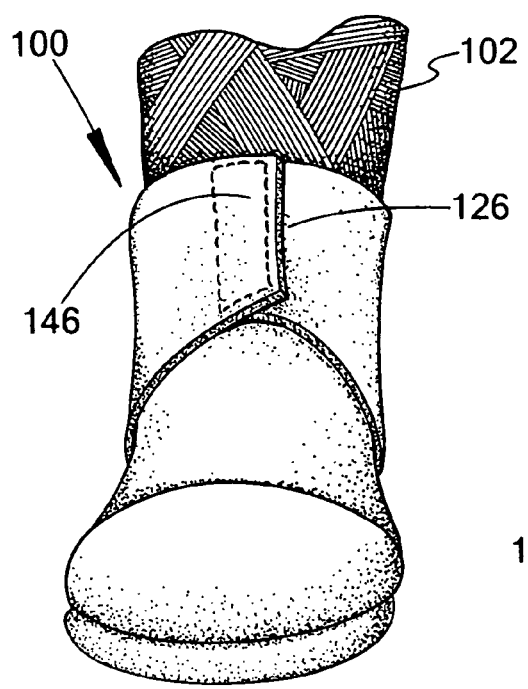
FIG. 1 depicts a front perspective view of protective and insulating cast cover 100 of this invention.
Figure 2:
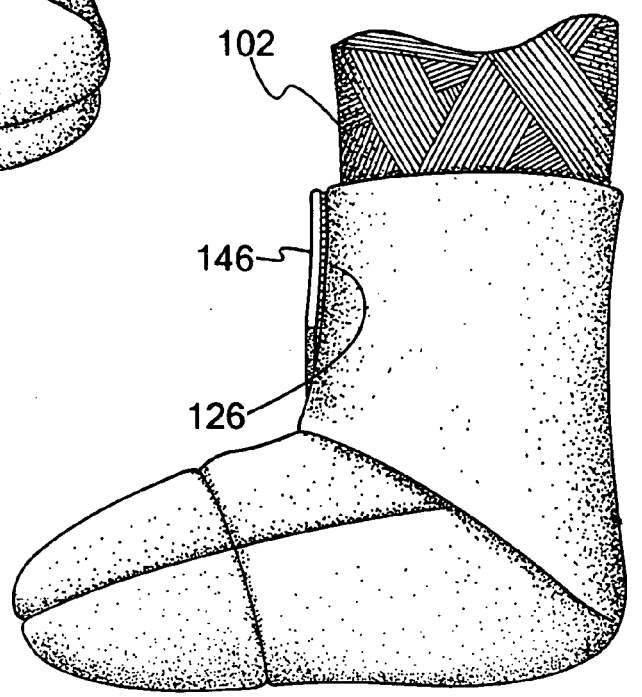
FIG. 2 depicts a side view of protective and insulating cast cover 100 of this invention.
Figure 3:
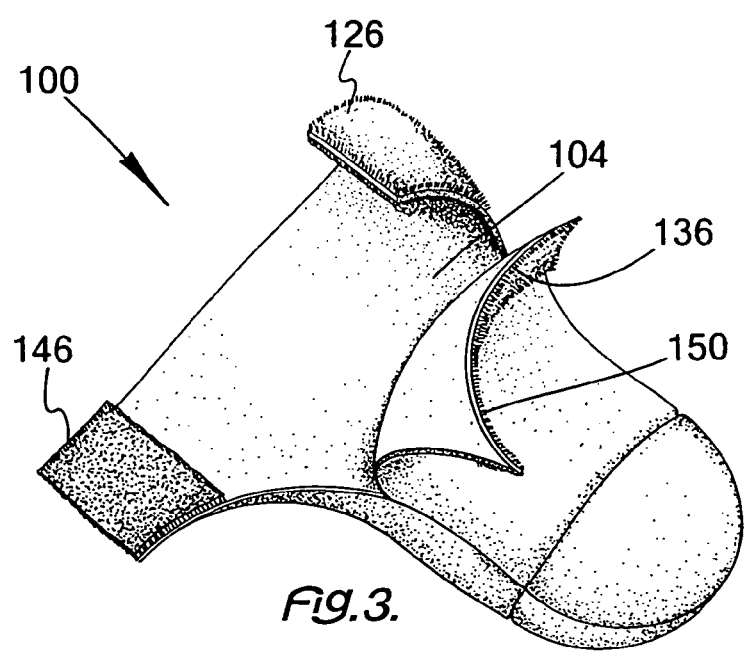
FIG. 3 depicts a top perspective view of protective and insulating cast cover 100 of this invention.

Referring now to FIG. 1, FIG. 2, and FIG. 3, a protective and insulating cast cover 100 is placed over a limb in a cast 102. The cast cover 100 is composed of material 104 that is both insulating and elastic. The insulating nature of the material 104 ensures that exposed areas of the limb will be protected from inclement weather.

The difference between FIG. 1 and FIG. 3 is in the tab position. Top ankle tab 146 and bottom ankle tab 126 can secured to each other in FIG. 1. In FIG. 3, on the tongue 136 is hook and loop assembly 150 to receive top ankle tab 146 and bottom ankle tab 126.

Figure 4:
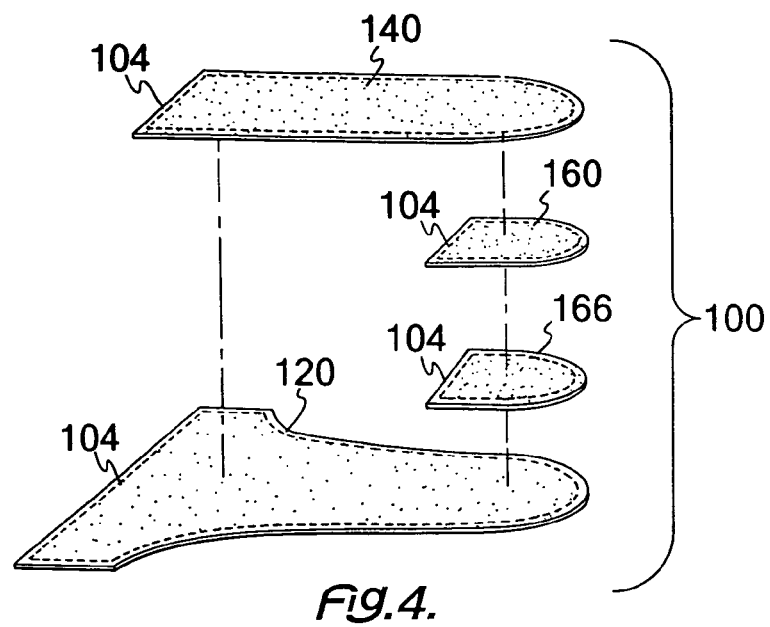
FIG. 4 depicts an exploded view of protective and insulating cast cover 100 of this invention

Referring now to FIG. 4, both the protective and insulating nature of cast cover 100 become clear. A majority of the cast is covered by a single piece of the material 104. This covering helps to keep the cast clean and dry and also serves a decorative purpose. Top toe panel 160 in top panel 140 and bottom toe panel 166 in bottom panel 120 provide and extra layer of protection and insulation for the exposed areas of the limb.

Figure 5:
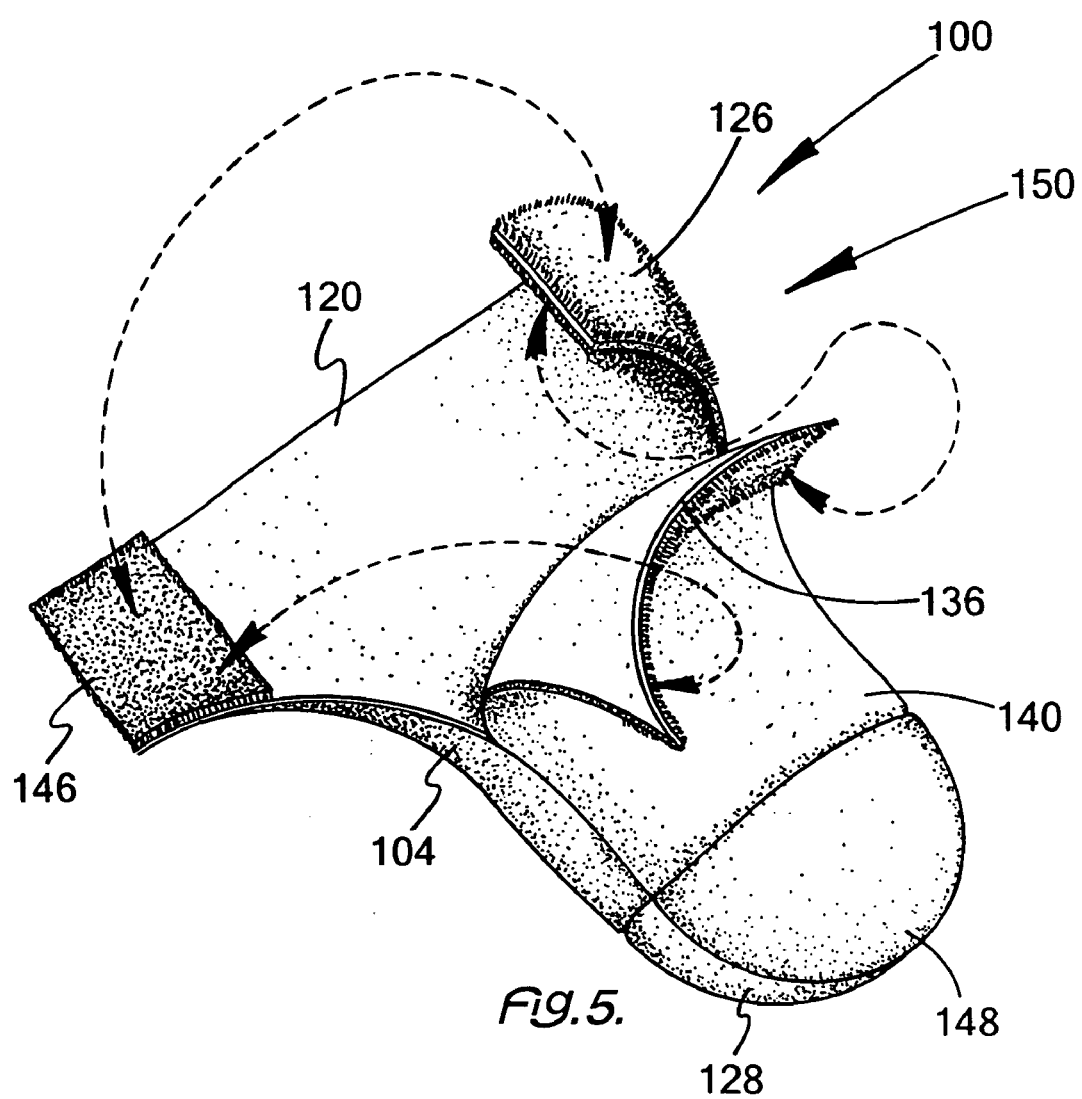
FIG. 5 depicts a top perspective view of protective and insulating cast cover 100 of this invention showing the hook and loop assembly 150.

Referring now to FIG. 5, one feature of cast cover 100 is the hook and loop assembly 150. The flexible nature of the material 104 and the hook and loop assembly 150 make it easy to put on and remove the cover and thus, reduce foot movement and pain in the process. The hook and loop assembly 150 can be undone to provide maximum room for sliding into or removing cast cover 100. Furthermore, the elasticity of the material 104 means that the cover 100 can be stretched to accommodate different sizes of cast 106. Bottom ankle tab 126 and top ankle tab 146 can be adjusted as fasteners on tongue 136 to ensure a snug fit around the ankle. Thus, cast cover 100 is well fitted and not bulky or unsightly.

Top panel 140 includes top ankle tab 146 with top toe end 148 oppositely disposed therefrom. Likewise, bottom panel 120 has bottom ankle tab 126 with bottom toe end 128 oppositely disposed therefrom. Top ankle tab 146 and bottom ankle tab 126 can secure to each other (FIG. 5) or to the tongue 136 if desired and hook and loop assembly 150 is present (FIG. 3).

Figure 6:
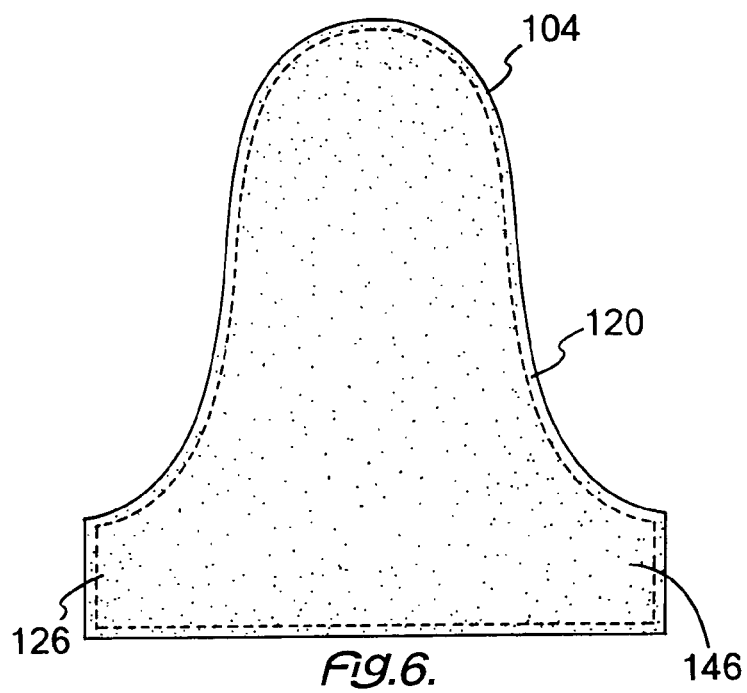
FIG. 6 depicts a bottom plan view view of bottom panel 120 for protective and insulating cast cover 100 of this invention.
Figure 7:
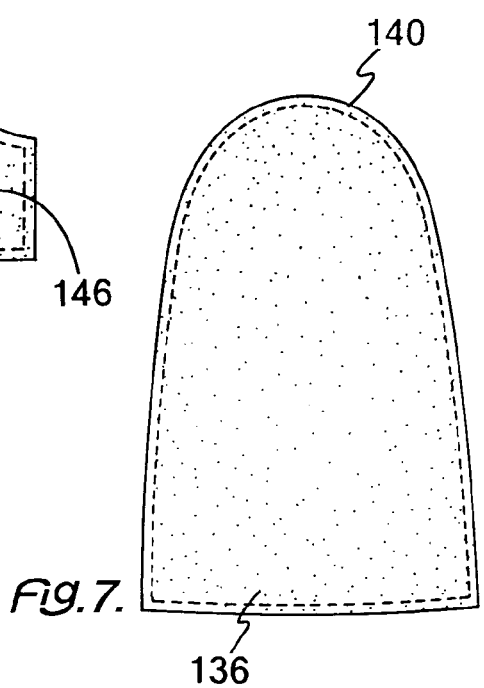
FIG. 7 depicts a top plan view of top panel 140 for protective and insulating cast cover 100 of this invention.

Referring now to FIG. 6 and FIG. 7, bottom panel 120 and top panel 140 adds to the well fitting nature of cast cover 100. Bottom panel 120 is designed to allow the material 104 to adjust to the contour of the heel. Top panel 140 allows cast cover 100 to adjust to the curves on the top portion of the limb. Therefore, cast cover 100 is decorative instead of bulky and unsightly. Furthermore, there is not an excess of material that can cause tripping or injury.

For example, when the limb is a foot, bottom panel 120 extends over the sole of the foot and up the heel. The top panel 140 extends over the foot with the tongue 136 extending up the shin. Bottom ankle tab 126 and top ankle tab 146 reach over tongue 136 and are secured thereto or to each other by hook and loop assembly 150 (FIG. 5).

Figure 8:
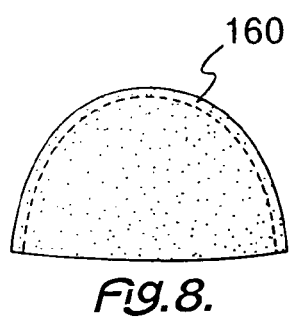
FIG. 8 depicts a top plan view of top toe panel 160 for protective and insulating cast cover 100 of this invention.
Figure 9:
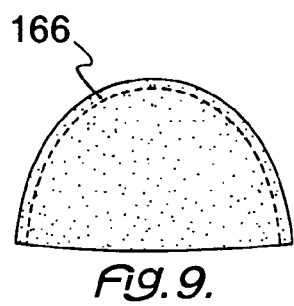
FIG. 9 depicts a bottom plan view of bottom toe panel 166 for protective and insulating cast cover 100 of this invention.

Referring now to FIG. 8 and FIG. 9, the extra insulation and protection from top toe panel 160 and bottom toe panel 166 become clear. Both top toe panel 160 and bottom toe panel 166 are secured Top Side of Cover 162, Bottom Side 164 Bottom Toe Panel: 166 This added layer helps to ensure that exposed areas of the limb stay clean, warm, and dry.

Figure 10:
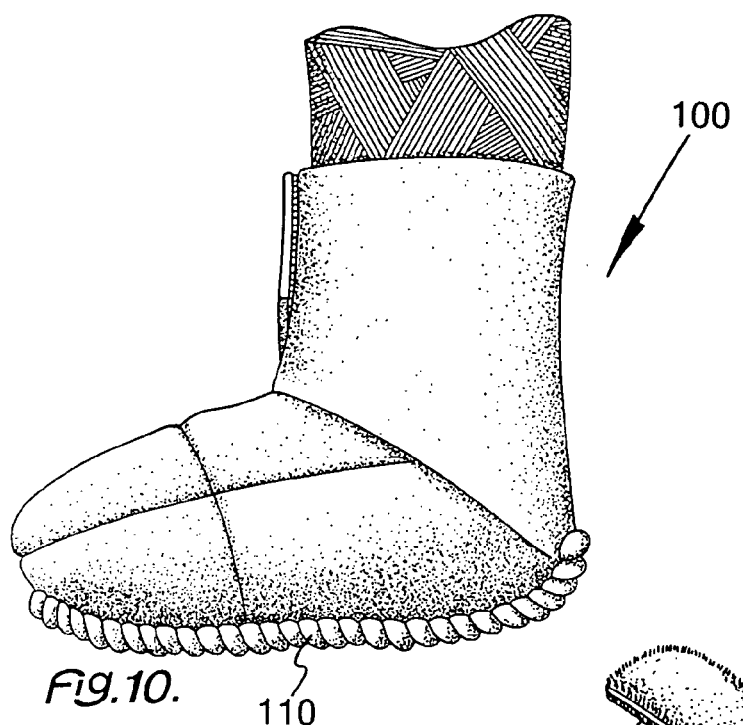
FIG. 10 depicts a side view of protective and insulating cast cover 100 of this invention with the rubber sole 110 option included.

With FIG. 10, the optional form, a rubber sole 110 is incorporated into the bottom of the cast cover 100. The rubber sole 110 provides traction, durability, and extra protection on the bottom of cast cover 100. Thus, a person who is able to walk on the injured limb can use the invention on outdoor, rough, or slick surfaces without risking further injury.

Figure 11:
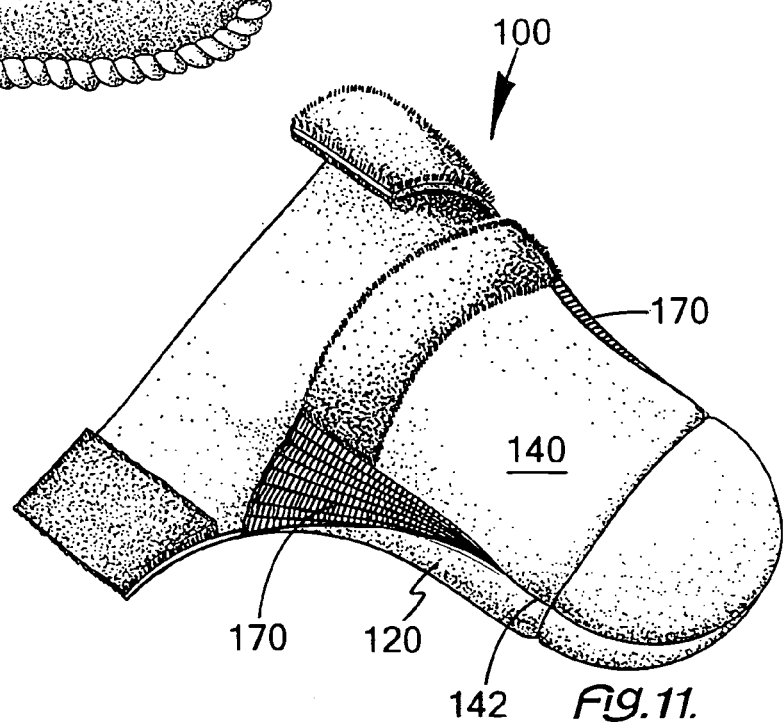
FIG. 11 depicts a top perspective view of protective and insulating cast cover 100 of this invention with an elastic panel 170.

With FIG. 11 protective and insulating cast cover 100 includes an elastic panel 170 extending partially along the area, where bottom panel 120 and top panel 140 separate at panel seam 142. Elastic panel 170 combines with the stretchable material of protective and insulating cast cover 100 in order to an even greater ease putting on or taking off the same.

Figure 12:
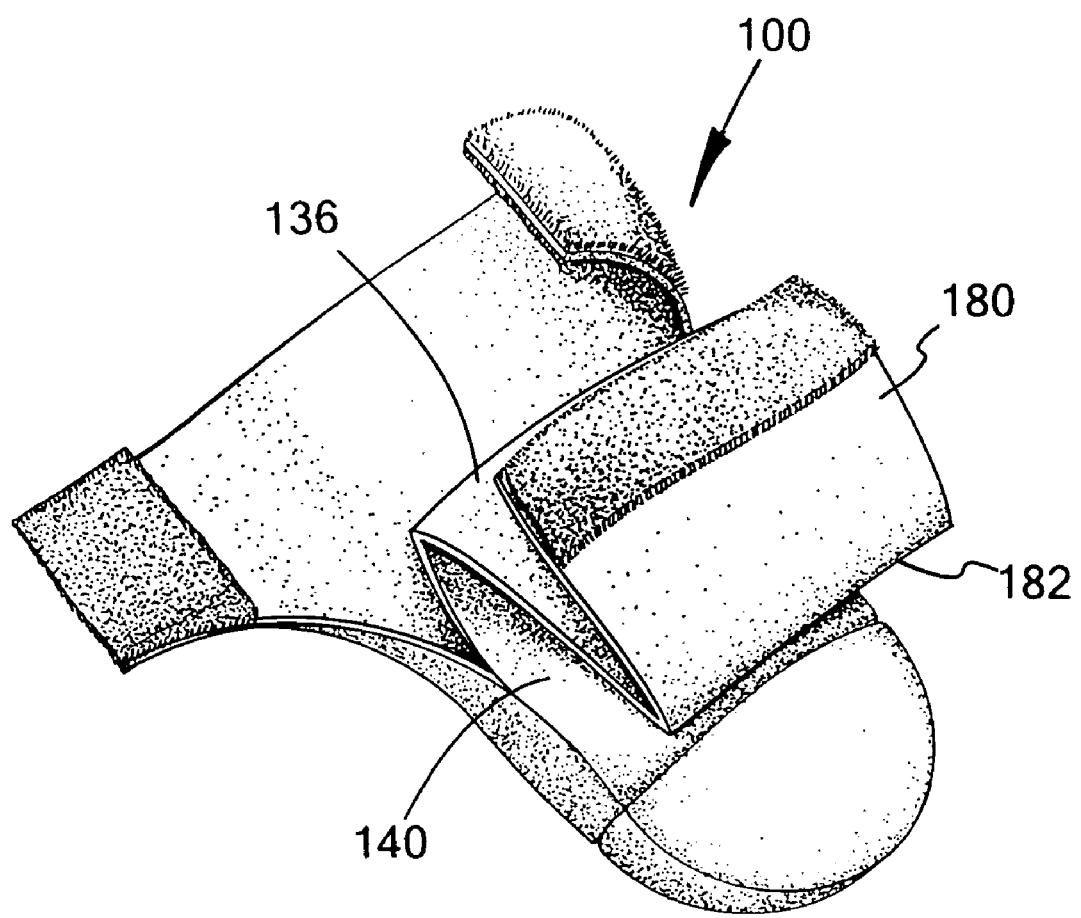
FIG. 12 depicts a top perspective view of protective and insulating cast cover 100 of this invention extended into a foldable tongue panel 180.

In FIG. 12, tongue 136 of top panel 140 is extended into a foldable tongue panel 180. Pleat 182 adds more material and padding for the top of protective and insulating cast cover 100. Thus, increased protection is added to the limb protected thereby.

This application—taken as a whole with the abstract, specification, claims, and drawings being combined—provides sufficient information for a person having ordinary skill in the art to practice the invention as disclosed and claimed herein. Any measures necessary to practice this invention are well within the skill of a person having ordinary skill in this art after that person has made a careful study of this disclosure.

Because of this disclosure and solely because of this disclosure, modification of this method and device can become clear to a person having ordinary skill in this particular art. Such modifications are clearly covered by this disclosure.

What is claimed and sought to be protected by Letters Patent of the United States is:

1. A protective and insulating cover for an injured limb comprising:
   (a) the protective and insulating cover having a bottom panel secured to a top panel;
   (b) the bottom panel being adapted to fit adjacent to a bottom of a limb;
   (c) the top panel being adapted to fit adjacent to a top of the limb;
   (d) the top panel having a tongue end oppositely disposed from a top toe end;
   (e) the bottom panel having a tab end oppositely disposed from a bottom toe end;
   (f) the top toe end being secured to the bottom toe end;
   (g) the tab end being releasably securable to the tongue end;
   (h) the tab end having a first fastening end oppositely disposed from a second fastening end; and
   (i) the tongue end receiving the first tab end and the second tab end in order to secure the protective and insulating cover over the injured limb;
   (j) the hook and loop assembly serving to fasten the first fastening end, the second fastening end, and the tongue together in a desired fashion;
   (k) the protective and insulating cover fitting over a cast on the injured limb;
   (l) the bottom panel having a length and a flexibility to fit over the limb;

(m) the limb being at least a foot and a heel;
(n) the bottom panel fitting over a bottom of the foot and the heel;
(o) the top panel fitting over a top of the foot and a shin extending therefrom;
(p) the top toe end and the bottom toe end including a reinforcing means;
(q) the reinforcing means including a top toe panel and a bottom toe panel;
(r) the top toe panel being secured at the top toe end;
(s) the bottom toe panel being secured at the bottom toe end;
(t) the top toe panel and the bottom toe panel serving to keep the toes of foot protected;
(u) the first fastening end being securable to at least one point selected from the group consisting of the second fastening end and the tongue;
(v) the second fastening end being securable to at least one point selected from the group consisting of the second fastening end and the tongue;
(w) the tongue being securable to at least one point selected from the group consisting of the second fastening end and the first fastening end; and
(x) a pleat being in the tongue.

* * * * *